US007550601B1

(12) United States Patent
Drake et al.

(10) Patent No.: US 7,550,601 B1
(45) Date of Patent: Jun. 23, 2009

(54) PREPARATION OF SUBSTITUTED-1,2,3-TRIAZOLES

(75) Inventors: Gregory W. Drake, Madison, AL (US); Gregory M. Kaplan, Palmdale, CA (US); Tommy W. Hawkins, Lancaster, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 505 days.

(21) Appl. No.: 11/203,578

(22) Filed: Aug. 15, 2005

(51) Int. Cl.
*C07D 249/04* (2006.01)
(52) U.S. Cl. ..................................................... 548/255
(58) Field of Classification Search .................. 548/255
See application file for complete search history.

(56) References Cited

U.S. PATENT DOCUMENTS 5,728,841 A * 3/1998 Shigeno et al. ............. 548/255

OTHER PUBLICATIONS

Collins, et al., J. Het. Chem, 2005, 42(1), pp. 19-27, especially p. 20.*

* cited by examiner

*Primary Examiner*—Golam M. M. Shameem
*Assistant Examiner*—Susannah Chung
(74) *Attorney, Agent, or Firm*—AMFCLO/JAZ; Thomas C. Stover

(57) ABSTRACT

The invention provides a high yield/isomerically pure synthesis of new 1-amino-3-substituted-1,2,3-triazolium salts and their subsequent transformation into isomerically pure 1-substituted-1,2,3-triazoles. These new 1-amino-3-substituted-1,2,3-triazolium salts are easily isolated and can be stored at ambient conditions with no degradation or isomerization. These quarternary salts are easily converted with appropriate silver salts to a wide array of new quarternary salts with various anions, with many of these new salts having melting points below 100 C, classifying them as ionic liquids. Subsequent diazotization of these 1-amino-3-substituted-1,2,3-triazolium salts results in high yields of isomerically pure 1-substituted-1,2,3-triazoles, that until this invention were problematic to make pure without tedious reagents or workup procedures. Both classes of materials (1-amino-3-substituted-1,2,3-triazolium salts as well as 1-substituted-1,2,3-triazoles) should be of high interest as these classes of materials are known to be very important pharmaceutical materials for a wide array of medical and agricultural applications as well as possible propellant applications.

2 Claims, No Drawings

PREPARATION OF SUBSTITUTED-1,2,3-TRIAZOLES

STATEMENT OF GOVERNMENT INTEREST

The invention described herein may be manufactured and used by or for the Government for governmental purposes without the payment of any royalty thereon.

RELATED PATENT APPLICATIONS

This invention relates generally to U.S. Pat. No. 6,509,473 B1, entitled Energetic Triazolium Salts by Greg W. Drake, issued 21 Jan. 2003.

FIELD OF THE INVENTION

This invention relates to preparation of triazoles, particularly preparation of substituted 1.2.3-Triazoles.

BACKGROUND OF THE INVENTION

The chemistry of N-substituted-1,2,3-triazoles has been well developed due to its high biological activity, however, the preparation of isomeric pure N-substituted-1,2,3-triazoles is not trivial. Direct alkylation of 1(H)-1,2,3-triazoles forms mixtures of 1- and 2-substituted 1,2,3-triazoles, which are often difficult to separate, and once formed often undergo isomerization equilibria in solution. Cycloaddition reactions usually lead to 1-substituted-1,2,3-triazoles. However, this synthesis route is complicated by the use of hazardous reagents, e.g., organic azides and acetylenic materials. High yields of 1-vinyl-1,2,3-triazole and 1-isopropyl-1,2,3-triazole have been reported, however the use of expensive 1(H)-1,2,3-triazole is required.

Heterocyclic compounds based on 1,2,3-triazoles have been widely employed due to their high biological activity, in antiviral, antimicrobial, antifungal medicines and agricultural chemicals. Other applications include photo-chemicals, corrosion inhibitors, and dyes. Previously, various routes for preparation of 1(H)-1,2,3-triazole have been reported. However, processes are complicated and overall yields are low. JP #05140121, 07278121, 07126257 and U.S. Pat. No. 5,478,947 describe the use of tosylhydrazide, glyoxal and ammonia to produce 1(H)1,2,3-triazole. The best reported overall yield is about 67%, however processes are very complicated and produce a lot of waste. U.S. Pat. No. 5,728,841 describes a method of preparing of 1(H)-1,2,3-triazole, through diazotization of 1-amino-1,2,3-triazole, however the best yield reported is 57%.

Recently, a patent application on new ionic liquids described the formation of 1-substituted-4-amino-1,2,4-triazolium salts from the alkylation of 4-amino-1,2,4-triazole with alkyl halides (Drake et al 2002). 1-amino-1,2,3-triazole is an isomer of 4-amino-1,2,4-triazole and it has been found to form a class of low melting salts many of which fit under the definition of ionic liquids. These ionic liquids have found a wide array of applications ranging from solvents and catalysts to energetic materials.

Heterocycles with high nitrogen content typically have high heats of formation, high densities, but can often have significant toxicities. Through the use of heterocyclic salt based materials, much of this toxicity can be significantly reduced for safer handling and exposure.

For the most pharmaceutical intermediates purity is a crucial factor, especially, when it comes to isomerical purity. Due to the completely different behavior of the different isomers in biological systems, preparation of desired isomers, not contaminated with other isomers is important. Preparation of isomerically pure N-substituted-1,2,3-triazoles is not trivial. Direct alkylation of 1(H)-1,2,3-triazoles forms mixtures of 1- and 2-substituted 1,2,3-triazoles, which are often difficult to separate, and once formed often undergo isomerization equilibria in solution. Cyclo-addition reactions usually lead to 1-substituted-1,2,3-triazoles, however this synthetic route is complicated by the use of hazardous explosive and sensitive reagents, e.g. organic azides and terminal acetylenes. U.S. Pat. No. 6,642,390 notes these drawbacks, but still employs organic azides in the synthesis of 1,2,3-triazole carboxylic acids. High yields of 1-vinyl-1,2,3-triazole, and 1-isopropyl-1,2,3-triazole have been reported, however the use of expensive 1(H)-1,2,3-triazole is required.

An object of the present invention is to provide a scalable process for preparing a novel class of 3-substituted-1-aminotriazolium salts and subsequently, 1-substituted-1,2,3-triazoles.

Accordingly, there is need and market for a low cost method of preparation of certain substituted triazoles which overcome the above prior art shortcomings.

There has now been developed a substituted triazolium salt, a new compound, and subsequently preparing therefrom 1-substituted-1,2,3-triazoles, a new method.

SUMMARY OF THE INVENTION

Broadly the present invention provides a new class of 1-amino-3-substituted-1,2,3-triazolium salts, represented by formula (I):

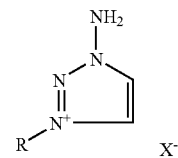

where R is either $C_1$-$C_{15}$ optionally substituted with halo, amino, nitro, hydroxyl, cyano, nitro or nitrate groups and $X^-$ is F, Cl, Br, I, carboxylate, nitrate, chlorate, perchlorate, dinitramide, nitrocyanamide, picrate, carboxylate, or phosphate.

These new salts can be prepared by alkylating 1-amino-1,2,3-triazole by corresponding compounds such as R—X as defined above.

Also provided is a method for preparing the salts of formula (I) above, by reacting 1-amino-1,2,3-trazole with alkylating agents in suitable solvents.

Further provided is a method of preparing the salts of formula (I), by introduction of selected anions by an anion exchange reaction.

Such salts are used in a new method to prepare 1-substituted-1,2,3-triazole comprising, by reacting salt (I) with $HNO_2$ and followed by consecutive neutralization by base in the polar solvent.

The invention further provides a method for expanding the class of salts via anion exchange into 1-amino-3-alkyl-1,2,3-triazolium salts where represented by formula (II):

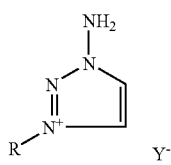

where R is either $C_1$-$C_{15}$ optionally substituted with halo, amino, nitro, hydroxyl, cyano, nitro, nitrate groups. Y is nitrate, perchlorate, dinitramide, nitrocyanamide, picrate, carboxylate, phosphate This invention further provides a method for highly selective preparation of 1-substituted-1,2,3-triazoles represented by formula (III)

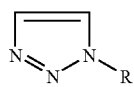

via diazotization of the abovementioned salts.

The compounds are useful in preparation of pharmaceutical and agricultural agents, also as highly energetic compounds for explosive, propellants and gas generating compositions and formulations.

DESCRIPTION OF PREFERRED EMBODIMENTS

Provided is an effective method to new classes of materials based on 1-amino-1,2,3-triazole through a facile synthesis route in high yields and purity. The following reactions serve to illustrate the versatility of the present invention.

General Procedure of Preparation of 1-amino-3-alkyl-1,2,3-triazolium Salts

Alkylation reactions were carried out in polar solvents, by reacting 1-amino-1,2,3-triazole and alkyl halide in the temperature range of 0° C. to 100° C. and the molar ratios ranges from 1 mole of 1-amino-1,2,3-triazole to 0.1-10.0 moles of alkyl halide, where the preferred ratio is 1 to 2, which insured complete conversion of 1-amino-1,2,3-triazole as well as decreasing the overall reaction time. The un-reacted alkyl halides and solvent are easily removed by vacuum distillation after reaction is complete and recovered to be reused. Higher temperatures >150° C. should not be employed, because it can lead to decomposition of starting 1-amino-1,2,3-triazole and some products, which can result in loss of yield and also increase the hazard of operations. While dialkylsylfates and nitrate esters can also be employed as alkylating agents, toxicity of dialkylsulfates and explosive properties of nitrate esters should be carefully considered. In most cases, when sulfate and/or nitrates are desired anions, simple halogen exchange can be a valuable option.

While acetonitrile is a preferred solvent for this process, those skilled in the art will recognize, that any solvents or mixtures, which do not react with the starting materials and dissolve them sufficiently can be employed.

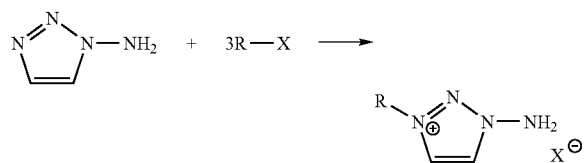

Reaction 1. The synthesis of 1-amino-3-alkyl-1,2,3-triazolium halide salts, where R=alkyl-, alkenyl-, alkynyl-, cyano-, alkylcyano-, alkylamine- etc. X=I, Br, Cl, $ONO_2$, sulfate, carbonate, etc.

After the reaction is complete, the products are easily separated by removal of solvents and unreacted materials by distillation, filtration or extraction. The 3-substituted-1-amino-1,2,3-triazolium salts are essentially pure and can be used without additional purification, or purified by conventional means i.e. crystallization, column chromatography etc.

2. Preparation of 1-amino-3-alkyl-1,2,3-triazolium Salts Via Anion Exchange.

Preparation of salts with anions other then halides can be achieved by halogen exchange reactions. Combining nitrogen-rich and highly energetic cations with strong oxidizing anions leads to formation of energetic salts with improved oxygen balance, which is an important property for use in applications such as explosives, monopropellants and gas generators. In cases where said salts require an additional amount of oxidizer to achieve the most complete decomposition with the release of maximum amount of gaseous products, these salts can be used as mixtures with known oxidizers such as, acids (nitric, perchloric etc.), salts (ammonium nitrate, ammonium dinitramide, ammonium perchlorate, hydroxyl-ammonium nitrate etc.) and non ionic organic compounds (HMX etc).

In a sample procedure, reaction of 1-amino-3-alkyl-1,2,3-triazolium chelates with a corresponding silver salt.

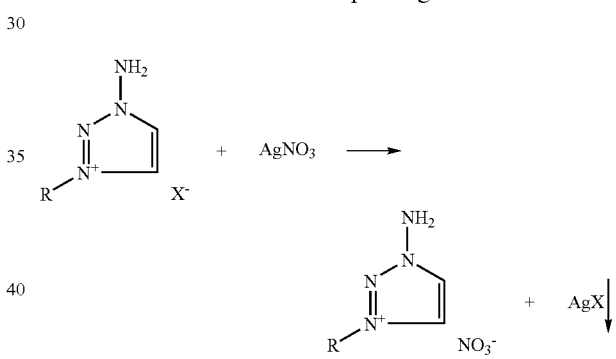

Reaction 2. Preparation of 1-amino-1,2,3-triazolium nitrates by halogen exchange Silver halides then can be isolated by filtration and solvent distilled off resulting in virtually quantitative yields of very pure 1-amino-3-alkyl-1,2,3-triazolium salts represented by formula (II). This method, while being simple and providing fast and convenient access to the numerous compounds on the lab scale, which is essential for the initial research, has its drawbacks. Required is the use of expensive and light sensitive silver salts. On a larger scale, use of acids, salts (other then silver) of said acids and use of ion-exchange resins and polymers, are preferred methods for producing such salts.

3. Preparation of Isomerically Pure 1-Substituted-1,2,3-triazoles.

The general procedure includes dissolving 1-amino-3-substituted-1,2,3-triazolium salts in water and reacting with $HNO_2$, which is prepared in situ from $NaNO_2$ and strong mineral acid. The amount of $HNO_2$ should be enough to complete the diazotization of 1-amino-3-substituted-1,2,3-triazolium salts preferably 1 mole per 1 mole. Slight excess of $HNO_2$ (1-5%) will benefit the process, as it insures a complete conversion of the starting material. However, a greater excess can result in extra cost associated with the raw materials. The process should be run at the temperature ranges 0° C.-20° C. to ensure the maximum yield of desired 1-substituted-1,2,3-triazoles.

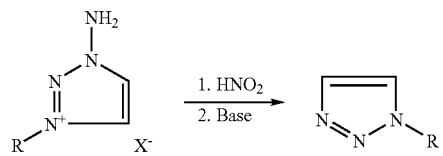

Reaction 3. The Synthesis of 1-substituted-1,2,3-triazoles where R=alkyl-, alkenyl-, alkynyl-, cyano-, alkylcyano-, alkylamine- etc. X=Br, Cl, ONO₂, sulfate, carbonate, etc.

After diazotization is complete, the reaction mixture is rendered alkaline by addition of base, preferably sodium bicarbonate. Products then extracted by suitable solvents, preferably ethyl acetate, and after solvent is removed by distillation, products which are essentially pure can be used without additional purification, or can be purified by conventional means, i.e., distillation etc. Multinuclear NMR reveals presence of two nonsymmetrical protons and also, nonsymmetrical carbons in the 1,2,3 triazole ring,

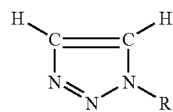

which is a strong indication of exclusive formation of 1-substituted 1,2,3-triazole.

The invention is further described in the following examples, which should not be construed in limitation thereof.

EXAMPLE 1

Preparation of 1-amino-1,2,3-triazole (1)

In a 500 ml round bottomed flask, equipped with an overhead stirrer 14.46 g (168 mmoles) of glyoxal bishydrazone were dispersed in 225 ml of acetonitrile at 20° C. Manganese dioxide 30.00 g (348 mmoles), was added portion-wise over a few minutes to the vigorously stirred solution. The reaction was stirred for 40 minutes whereupon additional manganese dioxide 20.00 g (232 mmoles) was added. Thin layer chromatography revealed the reaction was complete 20 minutes later and it was filtered through a plug of Celite. The filtrate was stripped down under reduced pressure leaving a viscous oil, that was sublimed yielding 12.30 g (88%) of highly pure 1-amino-1,2,3-triazole (1), mp 49-50° C.

EXAMPLE 2

Preparation of 1-amino-3-methyl-1,2,3-triazolium iodide (2a)

In a 100 ml flask, equipped with a magnetic stirrer, 2.00 g (23.8 mmoles) of 1-amino-1,2,3-triazole (1) was dissolved and stirred vigorously in 40 ml of acetonitrile at 20° C., whereupon methyl iodide 22.92 g (161.9 mmoles) was added. The reaction was stirred in darkness, being periodically monitored by thin layer chromatography until all 1-amino-1,2,3-triazole (1) was consumed. As the reaction progressed, white crystals of 1-amino-3-methyl-1,2,3-triazolium iodide (2a) precipitated. The product salt was filtered and washed with several aliquots (50 ml total) of diethyl ether. The mother liquor was concentrated by distillation under reduced pressure resulting in a second crop of crystals that were filtered, washed with diethyl ether combined with first crop and dried under high vacuum, resulting in a good yield of 4.99 g (93%) of 1-amino-3-methyl-1,2,3-triazolium iodide (2a), mp 146° C.

EXAMPLE 3

Preparation of 1-amino-3-ethyl-1,2,3-triazolium bromide (2b)

In a 100 ml glass reactor, equipped with a magnetic stirrer was placed 2.00 g (3.8 mmoles) of 1-amino-1,2,3-triazole (1) and dissolved in 40 ml of acetonitrile. To the reaction mixture was added 12.05 g (110.5 mmoles) of ethyl bromide and the reactor was sealed. The reaction mixture was stirred vigorously at 45° C. until all 1-amino-1,2,3-triazole was consumed. As the reaction progressed, white crystals of 1-amino-3-ethyl-1,2,3-triazolium bromide (2b) precipitated. The reaction mixture was cooled down to room temperature. The product salt was filtered and washed with several aliquots (50 ml total) of diethyl ether. The mother liquor was concentrated by distillation under reduced pressure, resulting in a second crop of crystals that were filtered, washed with diethyl ether, combined with the first crop and dried under high vacuum, resulting in a good yield of 3.82 g (83%) of 1-amino-3-ethyl-1,2,3-triazoliumbromide (2b), mp 117-118° C.

EXAMPLE 4

Preparation of 1-amino-3-n-propyl-1,2,3-triazolium bromide (2c)

In the same manner as above, 1-amino-1,2,3-triazole (1) 2.00 g (23.8 mmoles) was reacted with n-propyl bromide 13.60 g (110.6 mmoles) at 60° C., resulting in a good yield of 4.43 g (90%) of 1-amino-3-n-propyl-1,2,3-triazolium bromide (2c), mp 128-129° C.

EXAMPLE 5

Preparation of 1-amino-3-(2-propenyl)-1,2,3-triazolium bromide (2d)

In the aforementioned method, 1-amino-1,2,3-triazole (2) 5.00 g (59.5 mmoles) was reacted with allyl bromide 35.00 g (289 mmoles) at 20° C., and upon work-up resulted in a yield of 9.03 g (75%) of 1-amino-3-(2-propenyl)-1,2,3-triazolium bromide (2d), mp 100-101° C.

EXAMPLE 6

Preparation of 1-amino-3-n-butyl-1,2,3-triazolium bromide (2e)

Using the same method as previously mentioned, 1-amino-1,2,3-triazole (2) 2.00 g (23.8 mmoles) was reacted with n-butyl bromide (16.01 g., 116.8 mmoles) at 60° C. Upon work-up, 4.12 g (78%) of 1-amino-3-butyl-1,2,3-triazolium bromide (2e) was recovered, mp 131-132° C.

EXAMPLE 7

Preparation of 1-amino-3-methyl-1,2,3-triazolium nitrate (2a)

In a 100 ml flask 2.48 g (23.8 mmoles) of 1-amino-3-methyl-1,2,3-triazolium iodide (1a) was dissolved in 50 ml of methanol at 20° C. A solution of 1.86 g (1.5 mmoles) of silver nitrate in 50 ml of methanol was added during the 15 min period, under vigorous stirring in the darkness. Solid silver iodide immediately precipitated. The reaction was stirred for an additional hour, filtered though a celite plug and washed on a filter with an additional 50 ml of methanol. The Mother liquor was tested for residual silver and halogen. No silver or halogen was detected. The methanol was distilled off under reduced pressure, resulting in a good yield of 1.75 gm (91%) of 1-amino-3-methyl-1,2,3-triazolium nitrate mp 86-88° C.

EXAMPLE 8

Preparation of 1-amino-3-ethyl-1,2,3-triazolium Nitrate (2b)

In a manner similar to that for the 1-amino-3-methyl-1,2,3-triazolium iodide (1a) cited above, 1.84 g (9.5 mmoles) 1-amino-3-ethyl-1,2,3-triazolium bromide (1 b) was reacted with 1.62 g (9.5 mmoles) of silver nitrate, resulting in a excellent yield of 1.63 g (98%) of 1-amino-3-ethyl-1,2,3-triazolium nitrate (2b), mp 30-32° C.

EXAMPLE 9

Preparation of 1-amino-3-n-propyl-1,2,3-triazolium Nitrate (2c)

Using the same route as above 1-amino-3-n-propyl-1,2,3-triazolium bromide (1 c) 0.6 g (2.9 mmoles) was reacted with 0.5 g (2.9 mmoles) of silver nitrate resulting in excellent yield of 0.55 gm (99%) of 1-amino-3-n-propyl-1,2,3-triazolium nitrate (2c), mp 33-35° C.

EXAMPLE 10

Preparation of 1-amino-3-(2-propenyl)-1,2,3-triazolium Nitrate (3d)

Using the same method, 1-amino-3-(2-propenyl)-1,2,3-triazolium bromide (2) 3.05 g (14.9 mmoles) was reacted with 2.55 g (14.9 mmoles) of silver nitrate resulting in excellent yield of 2.71 gm (99%) of 1-amino-3-(2-propenyl)-1,2,3-triazolium nitrate (3d), mp 8-11° C.

EXAMPLE 11

Preparation of 1-amino-3-n-butyl-1,2,3-triazolium Nitrate (3e)

Using the same route, 1-amino-3-n-butyl-1,2,3-triazolium bromide (2) 3.36 g (15.2 mmoles) was reacted with 2.65 g (15.2 mmoles) of silver nitrate resulting in excellent yield of 3.08 gm (99%) of 1-amino-3-butyl-1,2,3-triazolium nitrate (3d), mp 48-50° C.

EXAMPLE 12

Preparation of 1-n-propyl-(1H)-1,2,3-triazole (3a)

1-amino-3-n-propyl-1,2,3-triazolium bromide (2c) 1.56 g (7.5 mmoles) was dissolved and stirred vigorously in 10 ml of water in a 50 ml round-bottomed flask, cooled in the ice-bath. Hydrochloric acid (37%), 1.56 g (7.5 mmoles) was added slowly to the vigorously stirred triazolium solution followed by the slow, drop-wise addition of $NaNO_2$ 0.556 g (8.1 mmoles) dissolved in 1 ml of water to the acidic solution of 3-amino-1-propyl-1,2,3-triazolium bromide (2c). After the addition was completed the reaction mixture was removed from the ice bath, stirred for 1 hour at room temperature and rendered alkaline by addition of $Na_2CO_3$, 4.5 g. The reaction mixture was extracted twice by 30 ml of ethyl acetate, the extracts were combined, dried over magnesium sulfate, and the ethyl acetate carefully distilled off under reduced pressure, yielding 0.72 g (87%) mmoles of 1-propyl-1,2,3-triazole (4a), bp 42° C.

EXAMPLE 13

Preparation of 1-(2-propenyl)(1H)-1,2,3-triazole (3b)

In the same manner as cited for the preceding 1-n-propyl-1,2,3-triazole (3a), 1-amino-3-(2-propenyl)-1,2,3-triazolium bromide (2d) 0.611 g (2.98 mmoles) was diazotized and upon workup provided an excellent yield of 0.292 g (90%). of 1-(2-allyl)-1,2,3-triazole (3b), bp 40° C.

EXAMPLE 14

Preparation of 1-n-butyl-(1H)-1,2,3-triazole (3c)

Using the method described above, 1-amino-3-n-butyl-1,2,3-triazolium bromide (2e) (1.62 g., 7.3 mmoles) was diazotized resulting in an excellent yield of 0.848 g (93%) of 1-butyl-1,2,3-triazole (3c), bp 58° C.

Accordingly, the present invention provides for the preparation of new triazolium salts, i.e., 1-amino-3-substituted-1,2,3-triazolium salts, e.g., per claim 1 herein.

The above triazolium salt of the invention is then reacted, e.g., with $HNO_2$ to provide the desired end-product, 1 substituted-1,2,3-triazole, by the novel method of the present invention.

The invention thus provides a method for preparation of 1-substituted-1,2,3-triazoles, which does not require the use of expensive 1(H)-1,2,3-triazole and proceeds very smoothly with almost quantitative yields via a two-step process. Used are 1-amino-1,2,3-triazole and corresponding alkylating agents as starting materials. Alkylating agents are inexpensive and commercially available, and 1-amino-1,2,3-triazole can be readily prepared by oxidation of glyoxal bishydrazone.

Prior to the present invention, 1,2,3-triazolium salts were extensively studied and reported, yet no reported attempts were made to prepare 3-substituted 1-amino-1,2,3-triazolium salts prior to the present invention. These materials can be widely used as valuable starting materials in various processes for preparing pharmaceutical intermediates and low melting salts or ionic liquids, which are now widely used as ionic solvents, catalysts etc.

Thus, the invention describes the high yield/isomerically pure synthesis of new 1-amino-3-substituted-1,2,3-triazolium salts and their subsequent transformation into isomerically pure 1-substituted-1,2,3-triazoles. These new 1-amino-3-substituted-1,2,3-triazolium salts are easily isolated and can be stored at ambient conditions with no degradation or isomerization. These quarternary salts are easily converted with appropriate silver salts to a wide array of new quarternary salts with various anions, with many of these new salts having melting points below 100 C, classifying them as ionic liquids. Subsequent diazotization of these 1-amino-3-substituted-1,2,3-triazolium salts, results in high yields of isomerically pure 1-substituted-1,2,3-triazoles, that until this invention were problematic to make pure without tedious reagents or work-up procedures. Both classes of materials (1-amino- 3-substituted-1,2,3-triazolium salts as well as 1-substituted-1,2,3-triazoles) should be of high interest as these classes of materials are known to be very important pharmaceutical materials for a wide array of medical and agricultural applications as well as possible propellant applications.

What is claimed is:

1. A compound consisting of the structural formula (I)

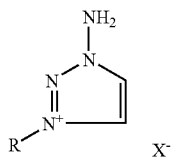

where R is $C_1$-$C_{15}$ alkyl, optionally substituted with halo, amino, nitro, hydroxyl, cyano, nitro or nitrate groups and X— is F, Cl, Br, I, carboxylate, nitrate, chlorate, perchlorate, dinitramide, nitrocyanamide, picrate, carboxylate or phosphate.

2. The compound of claim 1 having the structural formula:

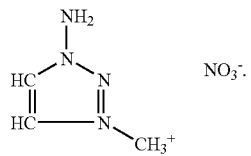

* * * * *